US012582319B2

(12) United States Patent
Cohen et al.

(10) Patent No.: US 12,582,319 B2
(45) Date of Patent: Mar. 24, 2026

(54) SMART TOOTHBRUSH THAT TRACKS AND REMOVES DENTAL PLAQUE

(71) Applicant: INTERNATIONAL BUSINESS MACHINES CORPORATION, Armonk, NY (US)

(72) Inventors: Guy M. Cohen, Ossining, NY (US); Lior Horesh, North Salem, NY (US); Raya Horesh, North Salem, NY (US); Amos Cahan, Dobbs Ferry, NY (US)

(73) Assignee: International Business Machines Corporation, Armonk, NY (US)

( * ) Notice: Subject to any disclaimer, the term of this patent is extended or adjusted under 35 U.S.C. 154(b) by 1239 days.

(21) Appl. No.: 16/823,436

(22) Filed: Mar. 19, 2020

(65) Prior Publication Data

US 2021/0290070 A1 Sep. 23, 2021

(51) Int. Cl.
*G16H 50/20* (2018.01)
*A46B 9/04* (2006.01)
(Continued)

(52) U.S. Cl.
CPC .............. *A61B 5/0088* (2013.01); *A46B 9/04* (2013.01); *A46B 13/02* (2013.01); *A46B 15/0022* (2013.01); *A46B 15/0036* (2013.01); *A46B 15/0038* (2013.01); *A46B 15/004* (2013.01); *A46B 15/0044* (2013.01);
(Continued)

(58) Field of Classification Search
CPC ..... A61B 5/0088; A61B 5/486; A61B 5/6887; A61B 2576/02; A63F 13/80; G16H 20/30; G16H 50/50; G16H 10/60; A46B 9/04; A46B 13/02; A46B 15/0022; A46B 15/0036; A46B 15/0038; A46B 15/004; A46B 15/0044; A46B 15/0046; G06T 7/0012; G06T 2207/30036
See application file for complete search history.

(56) References Cited

U.S. PATENT DOCUMENTS 5,894,620 A * 4/1999 Polaert ............... A46B 15/0002
433/29
6,485,300 B1 * 11/2002 Muller ................. A61B 5/0088
433/29
(Continued)

FOREIGN PATENT DOCUMENTS

CN 110213980 A * 9/2019 ............. A46B 15/00
CN 110769746 A * 2/2020 ........... A61B 5/0071
(Continued)

OTHER PUBLICATIONS

S. T. A. Aberin and J. C. d. Goma, "Detecting Periodontal Disease Using Convolutional Neural Networks," 2018, doi: 10.1109/HNICEM. 2018.8666389. (Year: 2018).*
(Continued)

*Primary Examiner* — Jason S Tiedeman
*Assistant Examiner* — Jonathan C Edouard
(74) *Attorney, Agent, or Firm* — Kristofer Haggerty

(57) ABSTRACT

The exemplary embodiments disclose an apparatus, a system and method, and a computer program product for removing dental plaque. The exemplary embodiments may include emitting light, detecting reflections of the light, analyzing the reflected light, and determining an amount or location of dental plaque based on the reflected light.

5 Claims, 6 Drawing Sheets

(51) Int. Cl.

| | | |
|---|---|---|
| *A46B 13/02* | (2006.01) | |
| *A46B 15/00* | (2006.01) | |
| *A61B 5/00* | (2006.01) | |
| *A63F 13/80* | (2014.01) | |
| *G06T 7/00* | (2017.01) | |
| *G16H 10/60* | (2018.01) | |
| *G16H 20/30* | (2018.01) | |
| *G16H 50/50* | (2018.01) | |

(52) U.S. Cl.

CPC .......... *A46B 15/0046* (2013.01); *A61B 5/486* (2013.01); *A61B 5/6887* (2013.01); *A63F 13/80* (2014.09); *G06T 7/0012* (2013.01); *G16H 10/60* (2018.01); *G16H 20/30* (2018.01); *G16H 50/50* (2018.01); *A61B 2576/02* (2013.01); *G06T 2207/30036* (2013.01)

(56) References Cited

U.S. PATENT DOCUMENTS

| | | | | |
|---|---|---|---|---|
| 8,214,958 | B2 * | 7/2012 | Pinyayev | A61B 5/0088 15/22.1 |
| 10,251,558 | B2 * | 4/2019 | Sumi | A61C 19/04 |
| 2005/0170316 | A1 | 8/2005 | Russell | |
| 2010/0311005 | A1 * | 12/2010 | Liang | G01B 11/2527 433/29 |
| 2011/0151409 | A1 * | 6/2011 | Binner | G01N 21/645 600/431 |
| 2015/0107034 | A1 * | 4/2015 | Shani | A46B 15/0006 15/22.1 |
| 2016/0166137 | A1 * | 6/2016 | Hakomori | A61C 1/088 433/29 |
| 2016/0242652 | A1 * | 8/2016 | Van Putten | A46B 15/0034 |
| 2017/0000352 | A1 * | 1/2017 | Deane | A61B 1/07 |
| 2018/0177575 | A1 | 6/2018 | Yoshida | |
| 2019/0167399 | A1 | 6/2019 | Kawabata | |
| 2019/0200746 | A1 * | 7/2019 | Serval | A61B 5/0077 |
| 2019/0328234 | A1 * | 10/2019 | Seibel | A61B 5/14539 |

FOREIGN PATENT DOCUMENTS

| | | | | | |
|---|---|---|---|---|---|
| DE | 4032779 | C2 * | 10/2000 | ........ | A46B 15/0002 |
| KR | 101162604 | B1 * | 7/2012 | | |
| WO | WO-2016051300 | A1 * | 4/2016 | ............ | A46B 13/02 |
| WO | WO-2016140199 | A1 * | 9/2016 | ........ | A46B 15/0036 |

OTHER PUBLICATIONS

Imangaliyev, Sultan, et al. Classification of Quantitative Light-Induced Fluorescence Images Using Convolutional Neural Network. arXiv:1705.09193, arXiv, May 25, 2017. arXiv.org, https://doi.org/10.48550/arXiv.1705.09193. (Year: 2017).*

CN-110213980-A—translated (Year: 2019).*

KR101162604B1—translated (Year: 2012).*

CN-110769746-A—translated (Year: 2020).*

WO-2016140199-A1—translated (Year: 2016).*

Mell et al., "The NIST Definition of Cloud Computing", National Institute of Standards and Technology, Special Publication 800-145, Sep. 2011, pp. 1-7.

Wikipedia, "Dental Plaque", https://en.wikipedia.org/wiki/Dental_plaque, printed Jan. 15, 2020, pp. 1-11.

\* cited by examiner

200

COMPUTER SYSTEM/SERVER 12

28

MEMORY

30 RAM

32 CACHE

34 SYSTEM STORAGE

40

42

16 PROCESSING UNIT

18

22 I/O INTERFACE(S)

20 NETWORK ADAPTER

24 DISPLAY

14 EXTERNAL DEVICE(S)

SMART TOOTHBRUSH THAT TRACKS AND REMOVES DENTAL PLAQUE

BACKGROUND

The exemplary embodiments relate generally to the cleaning of teeth, and more particularly to the cleaning of teeth with a smart toothbrush.

Dental plaque is a biofilm or mass of bacteria that grows on surfaces within the mouth. Dental plaque can lead to gingivitis (inflammation of the gums), periodontitis (infection of the gum that can lead to bone loss), and caries (acid demineralization of the enamel), among other conditions. Many people brush their teeth with the intention to remove dental plaque and minimize their chances of developing these conditions. However, many people develop conditions caused by dental plaque despite their teeth brushing efforts.

SUMMARY

The exemplary embodiments disclose an apparatus, a system and method, and a computer program product for removing dental plaque. The exemplary embodiments may include emitting light, detecting reflections of the light, analyzing the reflected light, and determining an amount or location of dental plaque based on the reflected light.

BRIEF DESCRIPTION OF THE SEVERAL VIEWS OF THE DRAWINGS

The following detailed description, given by way of example and not intended to limit the exemplary embodiments solely thereto, will best be appreciated in conjunction with the accompanying drawings, in which.

The drawings are not necessarily to scale. The drawings are merely schematic representations, not intended to portray specific parameters of the exemplary embodiments. The drawings are intended to depict only typical exemplary embodiments. In the drawings, like numbering represents like elements.

DETAILED DESCRIPTION OF THE SEVERAL VIEWS OF THE DRAWINGS

Figure 1:
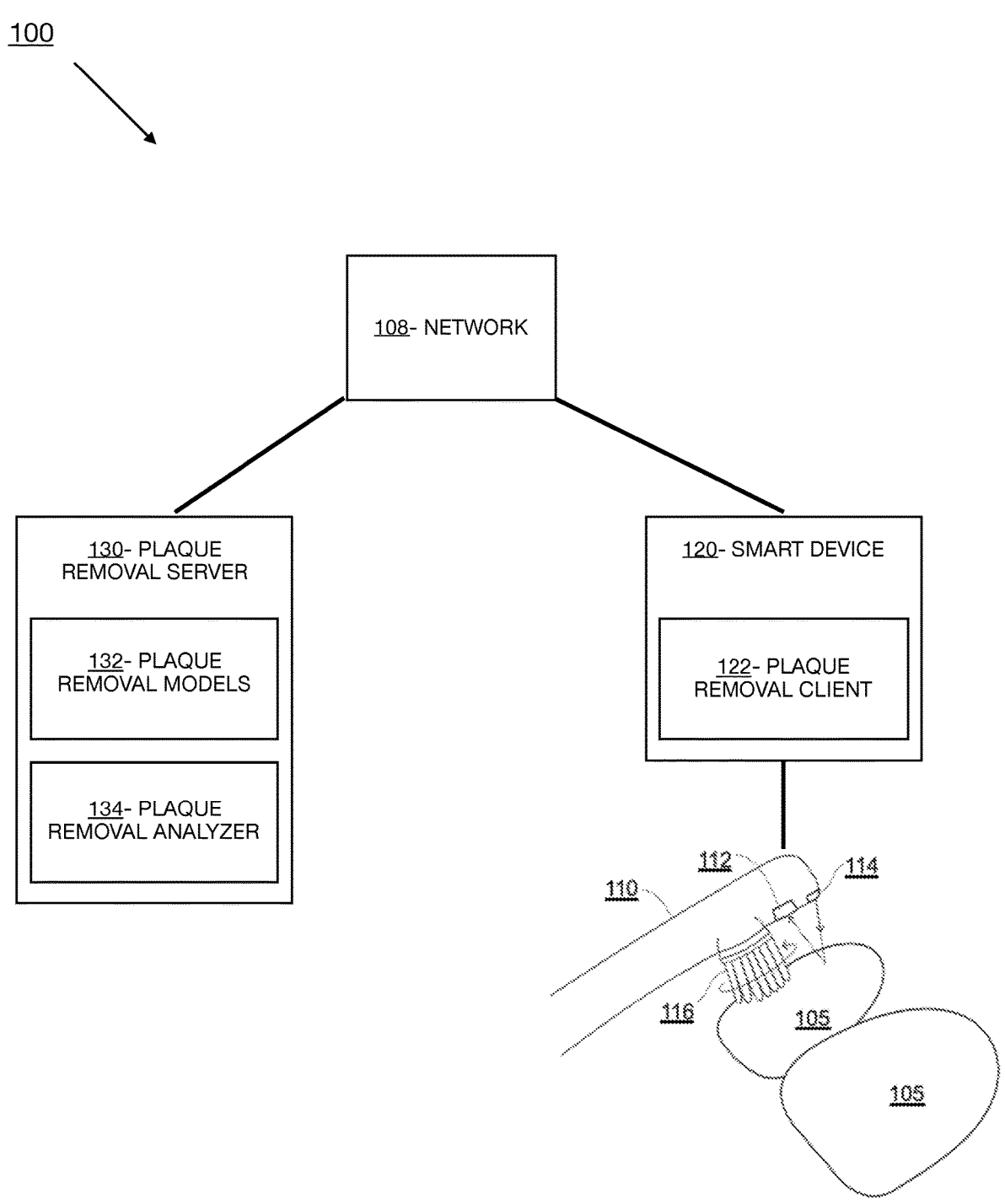
FIG. 1 depicts an exemplary schematic diagram of a plaque removal system 100, in accordance with the exemplary embodiments.

Detailed embodiments of the claimed structures and methods are disclosed herein; however, it can be understood that the disclosed embodiments are merely illustrative of the claimed structures and methods that may be embodied in various forms. The exemplary embodiments are only illustrative and may, however, be embodied in many different forms and should not be construed as limited to the exemplary embodiments set forth herein. Rather, these exemplary embodiments are provided so that this disclosure will be thorough and complete, and will fully convey the scope to be covered by the exemplary embodiments to those skilled in the art. In the description, details of well-known features and techniques may be omitted to avoid unnecessarily obscuring the presented embodiments.

References in the specification to "one embodiment", "an embodiment", "an exemplary embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described.

In the interest of not obscuring the presentation of the exemplary embodiments, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is focused on the distinctive features or elements according to the various exemplary embodiments.

Dental plaque is a biofilm or mass of bacteria that grows on surfaces within the mouth. Dental plaque can lead to gingivitis (inflammation of the gums), periodontitis (infection of the gum that can lead to bone loss), and caries (acid demineralization of the enamel), among other conditions. Many people brush their teeth with the intention to remove dental plaque and minimize their chances of developing these conditions. However, many people develop conditions caused by dental plaque despite their teeth brushing efforts.

Hence, a system is needed to address the aforementioned problem. Exemplary embodiments of the present invention disclose an apparatus, a method, and computer program product that will identify and remove plaque from teeth. Accordingly, example embodiments are directed to an apparatus that will identify and remove plaque from teeth. In general, it will be appreciated that embodiments described herein may relate to the removal of plaque from the teeth of any organism, or the removal of plaque from any surface. In embodiments, the apparatus may emit light and detect reflections of the light and/or properties thereof in order to generate brushing data corresponding to the teeth. In embodiments, audio, video, and other forms of data presentation methods may be used to guide a user while brushing so they will be able to more effectively remove plaque from their teeth, thereby improving on existing methods of brushing teeth. In particular, example embodiments may be configured for analyzing reflected light or changes in properties of the reflected light to determine one or more locations of plaque on a tooth or other surface, and for enhancing a user's tooth brushing experience. Use cases of embodiments described herein may relate to improvement of, for example, but not limited to, an enhancement of a tooth brushing experience in the removal of plaque from the teeth of a human or other entity by way of audio, video, text, virtual reality, augmented reality, diminished reality, etc. feedback to the user.

FIG. 1 depicts the plaque removal system 100, in accordance with the exemplary embodiments. According to the exemplary embodiments, the plaque removal system 100 may include a smart toothbrush 110, a smart device 120 and a plaque removal server 130, which may be interconnected via a network 108. While programming and data of the exemplary embodiments may be stored and accessed remotely across several servers via the network 108, programming and data of the exemplary embodiments may alternatively or additionally be stored locally on as few as one physical computing device or amongst other computing devices than those depicted.

In the exemplary embodiments, the network 108 may be a communication channel capable of transferring data between connected devices. Accordingly, the components of the plaque removal system 100 may represent network components or network devices interconnected via the network 108. In a preferred embodiment, the network 108 may be based on a local network protocol such as Bluetooth. While a cloud base connectivity may be enabled, the device may additionally be able to operate with full functionality when connectivity to the cloud is not available. Moreover, the network 108 may utilize various types of connections such as wired, wireless, free space optics, fiber optic, etc. In general, the network 108 may represent any combination of connections and protocols that will support communications between connected devices.

In the exemplary embodiments, the smart toothbrush 110 includes one or more optical sensors 112, one or more light sources 114, one or more bristles 116, and may include any other electronic device capable of computing, including receiving and sending data to and from other computing devices, in the removal of plaque from a tooth 105. While the smart toothbrush 110 is shown as a single device, in other embodiments, the smart toothbrush 110 may be comprised of a cluster or plurality of computing devices, working together or working independently. In some embodiments, the smart toothbrush 110 may include one or more storage mediums and act as a repository for brushing data of various forms, for example audio, video, text, etc. In addition, the smart toothbrush 110 may be configured for transferring brushing data to the smart device 120 and/or plaque removal server 130 via the network 108. The smart toothbrush 110 is described in greater detail as a hardware implementation with reference to FIG. 4, as part of a cloud implementation with reference to FIG. 5, and/or as utilizing functional abstraction layers for processing with reference to FIG. 6.

In the exemplary embodiments, the optical sensors 112 may be a light detector such as a p-i-n diode, a charge coupled device (CCD), camera/videocamera, or other devices capable of detecting light (photons) and converting the detected light into an electrical signal. The optical sensors 112 may detect light in the form of visible light (e.g., monochrome, broad spectrum, etc.), near-infrared, etc. In embodiments, the optical sensors 112 may be integrated with the smart toothbrush 110 and, for example, be detected through one or more bristles 116. The optical sensors 112 are described in greater detail with respect to FIGS. 2-3.

In the exemplary embodiments, the light sources 114 may be a light emitting diode (LED), laser, fluorescent light, or other light emitting devices. The light may be in the form of visible light (e.g., monochrome, broad spectrum, etc.), near-infrared, etc. In embodiments, the light sources 114 may be integrated with the smart toothbrush 110 and, for example, be emitted through one or more bristles 116. The light sources 114 are described in greater detail with respect to FIGS. 2-3.

In the example embodiment, the smart device 120 includes a plaque removal client 122, which is capable of preforming computations including receiving and sending data to and from other computing devices. In embodiments, the smart device 120 may be comprised of a cluster or plurality of computing devices, in a modular manner, etc., working together or working independently. In a preferred embodiment, smart device 120 includes a digital signal processor that is used to analyze data emitted from the light sources 114 and detected by the optical sensors 112. Such an analysis may include one or more methods such as signal filtering, fast Fourier transform (FFT), matched filter analysis, spectral analysis, etc. Smart device 120 may also include a digital signal processor to control the light source 114 such that modulation is applied to the light. The smart device 120 is described in greater detail as a hardware implementation with reference to FIG. 4, as part of a cloud implementation with reference to FIG. 5, and/or as utilizing functional abstraction layers for processing with reference to FIG. 6.

The plaque removal client 122 may act as a client in a client-server relationship with the plaque removal server 130 and may be a software and/or hardware application capable of communicating with and providing a user interface for a user to interact with a server via the network 108. Moreover, in the example embodiment, the plaque removal client 122 may be capable of transferring data from the smart device 120 to other devices such as the plaque removal server 130 or smart toothbrush 110 via the network 108. In embodiments, the plaque removal client 122 utilizes various wired and wireless connection protocols for data transmission and exchange, including Bluetooth, 2.4 gHz and 5 gHz internet, near-field communication, Z-Wave, Zigbee, etc. The plaque removal client 122 is described in greater detail with respect to FIG. 4-6.

In the exemplary embodiments, the plaque removal server 130 may include one or more plaque removal models 132 and a plaque removal analyzer 134, and may act as a server in a client-server relationship with the plaque removal client 122. The plaque removal server 130 is a computational device which may be a user's smart phone or tablet. The plaque removal client 122 may transfer data from the smart toothbrush 110 to the plaque removal server 130 for additional functions that cannot be efficiently performed on the smart device 120 and/or the smart toothbrush 110. While the plaque removal server 130 is shown as a single device, in other embodiments, the plaque removal server 130 may be comprised of a cluster or plurality of computing devices, working together or working independently. The plaque removal server 130 is described in greater detail as a hardware implementation with reference to FIG. 4, as part of a cloud implementation with reference to FIG. 5, and/or as utilizing functional abstraction layers for processing with reference to FIG. 6.

The plaque removal models 132 may be one or more algorithms modelling a correlation between one or more features extracted from brushing data and an amount of plaque present on a tooth. In the example embodiment, the plaque removal models 132 may be generated using machine learning methods, such as neural networks, deep learning, hierarchical learning, Gaussian Mixture modelling, Hidden Markov modelling, K-Means, K-Medoids, Fuzzy C-Means learning, etc., and may use features such as total light absorption, absorption features in the reflected light spectrum, bristle life/effectiveness, etc., as well as historical data such as brushing history, plaque accumulation patterns, locations of plaque, amounts of plaque, effectiveness of brushing, efficiency of brushing, etc. In embodiments, the plaque removal models 132 may weight the features based on an effect that the features have on the detection and/or amount of plaque such that features determined to be more associated with the detection/amount of plaque are weighted more than those that are not. The plaque removal models 132 are described in greater detail with reference to FIG. 2.

In the exemplary embodiments, the plaque removal analyzer 134 may be a software and/or hardware program capable of receiving a configuration and tooth brushing data. The plaque removal analyzer 134 may be capable of extracting features from the received tooth brushing data. Moreover, the plaque removal analyzer 134 may be capable of applying a model to the features to determine whether plaque has been detected on a tooth. The plaque removal analyzer 134 is described in greater detail with reference to FIG. 2.

Figure 2:
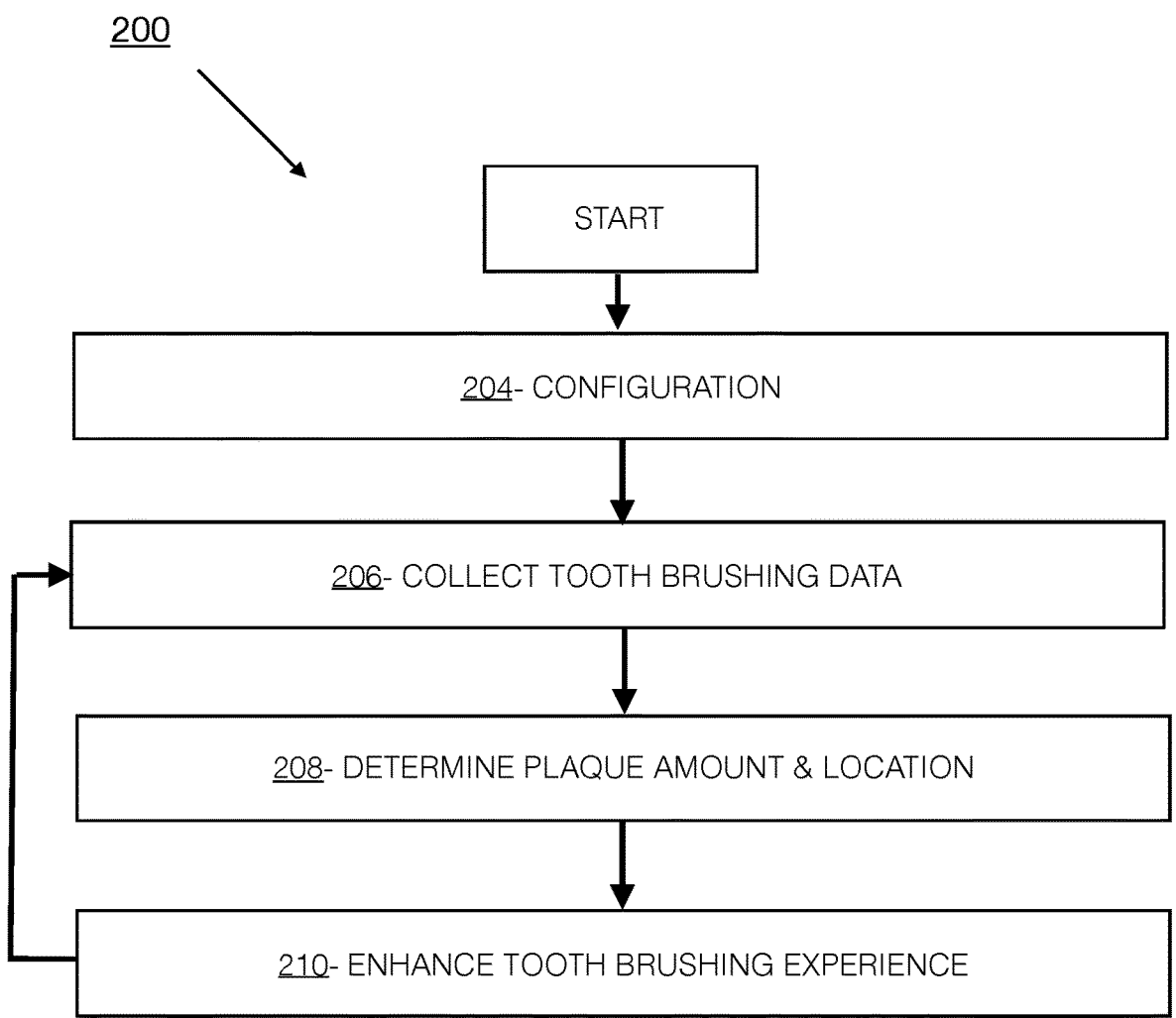
FIG. 2 depicts an exemplary flowchart 200 illustrating the operations of a plaque removal analyzer 134 of the plaque removal system 100 in identifying and removing dental plaque, in accordance with the exemplary embodiments.

FIG. 2 depicts an exemplary flowchart 200 illustrating the operations of the plaque removal analyzer 134 of the plaque removal system 100 in identifying and removing plaque, in accordance with the exemplary embodiments. For illustrative purposes throughout the FIG. 2 discussion, reference may be made to FIG. 3, which depicts an exemplary smart toothbrush 110.

The plaque removal analyzer 134 may receive a configuration (step 204). The plaque removal analyzer 134 may be configured by receiving a user registration and user preferences. In the example embodiment, the configuration may be received by the plaque removal analyzer 134 via the plaque removal client 122 and the network 108, for example via login credentials, reference to an internet protocol (IP) address or media access control (MAC) address, etc. In embodiments, receiving a user registration may involve receiving information such as a name, username, a type of the smart device 120, type of the smart toothbrush 110, the type of bristle module, type of optical sensors 112, type of light sources 114, a serial number of smart device 120, a serial number of smart toothbrush 110, serial numbers of optical sensors 112, user dental history, user brushing history, bristle age/last replacement date, and the like. Receiving a user registration may also involve receiving or extracting data from databases such as a user's dental records, brushing records, etc. User registration may be especially significant in any embodiments where a toothbrush or toothbrush base is shared among multiple users. For example, a family may have multiple members who share a toothbrush base, but each have their own toothbrush that mount to the shared toothbrush base.

During configuration, the plaque removal analyzer 134 may further receive user preferences (step 204 continued). User preferences may include an option indicating how plaque locations are conveyed to a user, for example via auditory signal, change in motor speed, vibration, lighting effects, push notification to the smart device 120, video recording, etc. A user preference may indicate any method of guiding a user to a location to brush based on the location of dental plaque. User preferences may also include the one or more preferred sizes and colors of visual notification, as well as the preferred frequency and amplitude of any preferred audio notification. These various settings include color, size, frequency, amplitude, etc., and may be customized to vary for different forms of enhancement for the user's brushing experience. The user preference may also include basic brushing preferences such as speed of brushing, agitation power, duration of brushing, etc.

To further illustrate the operations of the plaque removal analyzer 134, reference is now made to an illustrative example where a user registers their name, type of smart device 120, type of smart toothbrush 110, optical sensors 112, and light sources 114 via the plaque removal client 122 and the network 108. The user also uploads a link to their dental history and brushing history.

The plaque removal analyzer 134 may collect tooth brushing data (step 206). In embodiments, tooth brushing data may include a difference between an amount/type of emitted light and an amount/type of reflected light from a tooth as measured by one or more optical sensors 112. In embodiments, tooth brushing data may also include an intensity of reflected light, a scattering pattern of reflected light, a wavelength spectrum of reflected light, or a polarization of reflected light. In embodiments, the plaque removal analyzer 134 may collect tooth brushing data by first emitting a light towards a tooth 305 via the light sources 114 (see FIG. 3). The light may be emitted in visible (e.g., monochrome, broad spectrum, etc.), near-infrared, etc., to the tooth 305 directly from the light sources 114 or via the bristles 302. The plaque removal analyzer 134 may then detect an amount, type, pattern, frequency, etc. at which the light is reflected off of the tooth 305 via the optical sensors 112. The plaque removal analyzer 134 may then deduce an amount of plaque on the tooth 305 in that location based on analyzing the difference between the emitted light and the reflected light in conjunction with the plaque removal models 132, as will be described in greater detail forthcoming. In some embodiments, the plaque removal analyzer 134 may implement a camera as the light source 114 and/or optical sensors 112 and, rather than receiving tooth brushing data in the form of reflected light, receive tooth brushing data in the form of video or images.

The tooth brushing data may additionally include data from a user's dental history or brushing history, which may be received by the plaque removal analyzer 134 during configuration (step 206 continued). For example, the plaque removal analyzer 134 may collect tooth brushing data such as plaque accumulation patterns over time, past locations of plaque, past amounts or quantities of plaque, or an effectiveness or efficiency of brushing areas with plaque over time. Tooth brushing data may be collected in any form, and may be received from the smart toothbrush 110, the smart device 120, one or more optical sensors 112, one or more records or databases uploaded during configuration, and/or any other components or sources. In embodiments, one or more plaque disclosing agents, fluorescent agents, or additive colorings may be utilized in the collection of tooth brushing data.

With reference again to the previously introduced example where the user registers and configures their plaque removal system 100, the plaque removal analyzer 134 collects amounts of light, intensities of light, scatterings of light, wavelength spectrums of light, and polarizations of light of light sources 114 reflected back to optical sensors 112 by a tooth. The plaque removal analyzer 134 also collects the user's plaque accumulation patterns over time, past locations of plaque, past amounts or quantities of plaque, and an effectiveness of brushing areas with plaque over time from the user's dental history.

The plaque removal analyzer 134 may determine a plaque amount and/or location (step 208). In embodiments, the plaque removal analyzer 134 may extract features of one or more of a user's teeth (i.e., plaque) from the collected tooth brushing data, and may include light features such as an amount of light absorption (based on the reflected light intensity), light scattering, light wavelength spectrum, and light polarization. Additional features may include brushing history features such as plaque accumulation patterns, locations of plaque, amounts of plaque, effectiveness of brushing, and efficiency of brushing, etc. With respect to light features, the plaque removal analyzer 134 may extract a feature with respect to the reflected light of a tooth from one or more optical sensors 112 and/or light sources 114. The plaque removal analyzer 134 may extract light features in real-time as a user is brushing their teeth. In one embodiment, the plaque removal analyzer 134 may conclude that a surface is clean of plaque by measuring a reflected signal intensity over time and observing when the signal plateaued. When the signal does not change over time (plateaued), it suggests that most of the plaque was removed and that additional brushing would have little benefit. When a fluorescent dye is used, the disappearance of the fluorescence may be an indication that the surface is now clean of plaque. There are several methods that may be used to separate the transmitted light from the reflected light collected from the tooth surface. When a dye is used, the wavelength of the transmitted light is shorter than that the wavelength of the reflected light. In one example, the transmitted light is in the UV (~380 nm) and the reflected light is in the visible or near infared (IR). A filter that blocks the transmitted light wavelength is placed before the optical sensor 112. This allows only the reflected light to be measured. When the transmitted light and reflected light are in the same wavelength, light polarization and/or scattering angle is used to distinguish between the transmitted light and reflected light. For example, the transmitted light may have a linear polarization in the vertical orientation, and a filter (polarizer) that passes light polarized in the horizontal orientation may be placed before the optical sensor 112. The unpolarized reflected light would also include some light in the horizontal orientation. Therefore, light collected at a different polarization than transmitted light is reflected light. When the transmitted light is white (contains a broad spectrum of wavelength), the reflected light will be attenuated at some wavelengths where the plaque absorbs light. By collecting scattered light and analyzing the spectrum, dips around the wavelengths where absorption occurs can identify a plaque "fingerprint," or location/amount. This can allow for distinguishing a non-plaque surface that may absorb light (for example a stain on the tooth surface) but is likely to have a different spectral fingerprint than that typical of plaque.

In addition to extracting light features, the plaque removal analyzer 134 may also extract brushing history features such as locations of plaque, amounts of plaque, plaque accumulation patterns, locations of fillings, locations of stains, discolorations of tooth surfaces, effectiveness of brushing, and efficiency of brushing (step 208 continued). The plaque removal analyzer 134 may extract brushing history features from one or more databases received during configuration. In embodiments, the plaque removal analyzer 134 may extract a location of plaque by identifying areas of one or more teeth where light absorption is high. The plaque removal analyzer 134 may extract an amount of plaque by identifying the amount of light absorption at a given area of a tooth. For example, the plaque removal analyzer 134 may determine that an area of a tooth with a higher amount of light absorption or other light features, has a larger quantity of plaque build-up than an area of a tooth with a lower amount of light absorption or other light features. The plaque removal analyzer 134 may extract a plaque accumulation pattern by monitoring the locations and amounts of plaque on a user's teeth over a period of time. For example, the plaque removal analyzer 134 may extract a plaque accumulation pattern if a user's teeth accumulated more plaque on the molars than on the incisors over the course of a month.

In addition to extracting features such as locations of plaque, amounts of plaque, and plaque accumulation patterns, the plaque removal analyzer 134 may additionally extract brushing history features such as an effectiveness of brushing and efficiency of brushing (step 208 continued). The plaque removal analyzer 134 may extract a user's effectiveness of brushing plaque by identifying a decrease in an amount of plaque in a given area of one or more teeth, or a decrease in the number of locations of plaque on the user's teeth. The plaque removal analyzer 134 may extract an efficiency of brushing plaque by comparing a user's effectiveness of brushing plaque to the amount of time that the user spends brushing their teeth. For example, the plaque removal analyzer 134 may determine that a first user who spends ten minutes per day brushing their teeth and now has significantly lower quantities of plaque on their teeth after one month is efficiently brushing plaque from their teeth. The plaque removal analyzer 134 may determine that a second user who spends twenty minutes per day brushing their teeth and now has minimally lower quantities of plaque on their teeth after one month is not efficiently brushing plaque from their teeth.

In embodiments, the plaque removal analyzer 134 may apply one or more models to the extracted features in determining an amount and/or location of plaque (step 208 continued). In embodiments, the plaque removal analyzer 134 may simply analyze the light features without applying a model. In other embodiments, the plaque removal analyzer 134 may apply the one or more plaque removal models 132 to the extracted features to compute a value indicative of an amount of plaque. As previously mentioned, such extracted features may include an amount of light absorption, light intensity, light scattering, light wavelength spectrum, light polarization, brushing history, plaque accumulation patterns, locations of plaque, amounts of plaque, effectiveness of brushing, and efficiency of brushing for the user. The one or more plaque removal models 132 may be generated through machine learning techniques such as neural networks. Moreover, the plaque removal analyzer 134 may weight the extracted features. In embodiments, the one or more plaque removal models 132 may be trained at initialization and/or during operation through the use of a feedback loop to weight the features such that features shown to have a greater correlation with plaque are weighted greater than those features that are not.

Based on the features identified in the data and the weightings assigned by the plaque removal models 132, the plaque removal analyzer 134 may determine and map an amount of plaque for any region of teeth (step 208 continued). For example, the features and weights may be represented by numeric values and the plaque removal analyzer 134 may multiply identified features by the weights to compute a plaque amount for each tooth. In embodiments, the plaque removal analyzer 134 may determine values indicative of amounts of plaque for various regions of a single tooth, for example a front, back, top, middle, or bottom of a tooth.

With reference again to the previously introduced example where the plaque removal analyzer 134 collects the user's tooth brushing data, the plaque removal analyzer 134 extracts an amount of light absorption, light intensity, light scattering, light wavelength spectrum, light polarization, brushing history, plaque accumulation patterns, locations of plaque, amounts of plaque, effectiveness of brushing, and efficiency of brushing for the user. The plaque removal analyzer 134 additionally applies the plaque removal models 132 to the extracted features to compute values indicative of amounts of plaque for each tooth in the user's mouth.

The plaque removal analyzer 134 may enhance a tooth brushing experience (step 210). The plaque removal analyzer 134 may enhance a tooth brushing experience by providing feedback to a user indicative of whether or not plaque has been detected and/or removed. In embodiments, providing feedback to a user may include guiding a user to a location to brush based on the one or more locations of dental plaque. Feedback may be provided in audio, video, touch, etc. form. For example, the plaque removal analyzer 134 may notify the user of the presence of plaque in an area of one or more of the user's teeth with a chime, a blinking light, or a change in motor speed of a toothbrush. In some embodiments, the plaque removal analyzer 134 may provide verbal or graphical instructions to the user to direct them to a plaque surface. For example, the plaque removal analyzer 134 may produce audio feedback: "Plaque has been identified on the back side of this tooth." In some embodiments, the plaque removal analyzer 134 may enhance a toothbrushing experience with gamification. For example, a user may accumulate credits or points for each plaque region that has been brushed, and may convert accumulated credits or points towards a reward. Additional forms of enhanced brushing experiences may include the recording of brushing sessions in text, audio, video, etc. form and sharing of recorded brushing sessions with medical and/or dental professionals. In embodiments, after enhancing a tooth brushing session, the plaque removal analyzer 134 may iterate steps 206 through 210 for the entirety of a brushing session. In some embodiments, the plaque removal analyzer 134 may iterate steps 206 through 210 until the smart toothbrush 110 or smart device 120 have been turned off. In some embodiments, the plaque removal analyzer 134 may determine that a tooth brushing session has been completed upon detecting audio, video, etc. indicators via one or more optical sensors 112 such as a user saying, "I'm done brushing for now" or "That's enough."

With reference again to the previously introduced example where the plaque removal analyzer 134 applies the plaque removal models 132 to the extracted features to compute values indicative of amounts of plaque for each tooth in the user's mouth, the plaque removal analyzer 134 emits the following audio message: "Plaque has been located on one of your molars. You will hear a beep when your brush is positioned to remove it."

Figure 3:
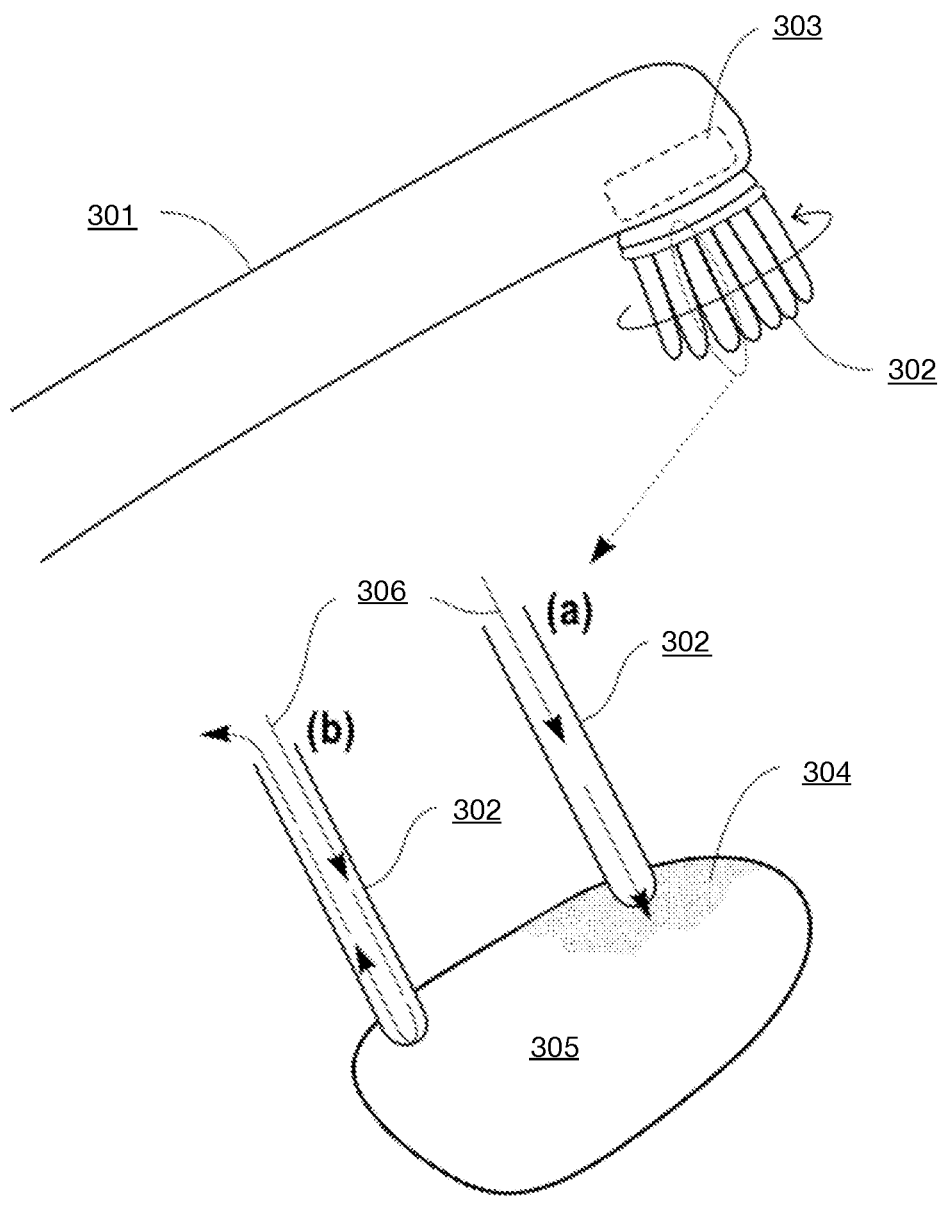
FIG. 3 depicts an illustrative example of the operations of a smart toothbrush 301 of the plaque removal system 100, in accordance with the exemplary embodiments.

FIG. 3 depicts an illustrative example of the smart toothbrush emitting light through its light guiding bristles 302 and detecting the amount of light reflected by a tooth 305 through its bristles 302 via one or more optical sensors 112, in accordance with the exemplary embodiments. In embodiments, the smart toothbrush may comprise an actuator that may rotate or translate the one or more bristles 302. With reference to FIG. 3, the present invention discloses a smart toothbrush 301 with bristles 302, one or more light sources and sensors 303, plaque 304, teeth 305, and light 306. The one or more light sources and sensors 303 may emit light 306T through the bristles 302. In embodiments, the one or more light sources 303 may emit one or more types of light from the group comprising monochromatic light, light having a plurality of wavelengths, white light, and colored light. In embodiments, the one or more light sources 303 may emit light that is polarized. In embodiments, the one or more light sources 303 may be one or more light emitting diodes (LEDs), lasers, or fluorescent lights. In embodiments, the one or more optical sensors 303 may be comprised of one or more diode photodetectors, charged couple device (CCD) photodetectors, or phototransistors.

With reference to 302 (*a*), the transmitted light 306T may be absorbed by plaque 304 on a tooth 305. With reference to 302 (*b*), the light 306T may be reflected (306R) by a clean tooth 305 and may travel back through the bristles 302 to be detected by the sensors 303. In some embodiments, the light 306T may be guided from the tooth 305 to the sensors 303 through the same bristle 302 that guided the light 306T from the light sources 303 to the tooth 305. In some embodiments, the light 306T may be guided from the tooth 305 to the sensors 303 through a different bristle 302 than the bristle that guided the light 306T from the light sources 303 to the tooth 305. In these embodiments, a first bristle 302 may guide the light 306T from the light sources 303 to the tooth 305, and a second bristle 302 adjacent or close to the first bristle 302 may guide the light 306R from the tooth 305 to the sensors 303. In some embodiments, a first bristle 302 may guide the light 306T from the light sources 303 to the tooth 305, one or more fluorescent agents attached to the plaque may be excited by the light 306T, and emit fluorescent light which may be collected as light 306R by a second bristle 302, and the second bristle 302 may guide the light 306R to the sensors 303. In some embodiments, a first bristle 302 may guide the light 306T from the light sources 303 to the tooth 305, and one or more plaque disclosing agents or additive colorings may absorb some or all of the light. Reflected light 306R may be collected by bristle 302, guide the light 306R back to the sensors 303.

The transmitted light 306T and reflected light 306R may be different. For example, transmitted light 306T may have a linear polarization, while the reflected light 306R is likely to be unpolarized. The unpolarized light 306R can be collected by the same bristle 302 (*a*) that guided light 306T or can be collected as scattered light by an adjacent bristle 302 (*b*). In the same example, light 306T may have linear polarization that is vertical. A polarizer (a filter that allows the passing of light with a specific polarization) allowing the passage of light with a horizontal linear polarization may be placed in front of the optical sensors 112. The polarizer thus allows the passing of reflected light 306R and blocks transmitted light 306T. In yet another embodiment, light 306T is of different wavelength than light 306R. This typically occurs when a fluorescent dye is used. The light 306T excites the fluorescent dye that is attached to plaque 304. The dye emits light 306R that is then collected by bristle 302 (*a*) or 302 (*b*). When a multi-colored light 306T is used, some spectral components of the light are absorbed in the plaque while other spectral components are absorbed by the clean tooth surface. The reflected light 306R thus provides a "fingerprint" of which surface the light was reflected from. Different spectral components may be used when multi-color or white light is used. The reflected light 306R which is scattered off the tooth 305 surface or the plaque 304 is typically collected by an adjacent bristle 302 (*b*).

Figure 4:
FIG. 4 depicts an exemplary block diagram depicting the hardware components of the plaque removal system 100 of FIG. 1, in accordance with the exemplary embodiments.

FIG. 4 depicts a block diagram of devices within the plaque removal analyzer 134 of FIG. 1, in accordance with the exemplary embodiments. It should be appreciated that FIG. 4 provides only an illustration of one implementation and does not imply any limitations with regard to the environments in which different embodiments may be implemented. Many modifications to the depicted environment may be made. In one embodiment, the plaque removal analyzer 134 processing capabilities may be embedded in the toothbrush's handle. In another embodiment, some of the processing capabilities may take advantage of a computational device like a smart phone which may be linked (Bluetooth or alike) to the toothbrush.

Devices used herein may include one or more processors 02, one or more computer-readable RAMs 04, one or more computer-readable ROMs 06, one or more computer readable storage media 08, device drivers 12, read/write drive or interface 14, network adapter or interface 16, all interconnected over a communications fabric 18. Communications fabric 18 may be implemented with any architecture designed for passing data and/or control information between processors (such as microprocessors, communications and network processors, etc.), system memory, peripheral devices, and any other hardware components within a system.

One or more operating systems 10, and one or more application programs 11 are stored on one or more of the computer readable storage media 08 for execution by one or more of the processors 02 via one or more of the respective RAMs 04 (which typically include cache memory). In the illustrated embodiment, each of the computer readable storage media 08 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Devices used herein may also include a R/W drive or interface 14 to read from and write to one or more portable computer readable storage media 26. Application programs 11 on said devices may be stored on one or more of the portable computer readable storage media 26, read via the respective R/W drive or interface 14 and loaded into the respective computer readable storage media 08.

Devices used herein may also include a network adapter or interface 16, such as a TCP/IP adapter card or wireless communication adapter (such as a 4G wireless communication adapter using OFDMA technology). Application programs 11 on said computing devices may be downloaded to the computing device from an external computer or external storage device via a network (for example, the Internet, a local area network or other wide area network or wireless network) and network adapter or interface 16. From the network adapter or interface 16, the programs may be loaded onto computer readable storage media 08. The network may comprise copper wires, optical fibers, wireless transmission, routers, firewalls, switches, gateway computers and/or edge servers.

Devices used herein may also include a display screen 20, a keyboard or keypad 22, and a computer mouse or touchpad 24. Device drivers 12 interface to display screen 20 for imaging, to keyboard or keypad 22, to computer mouse or touchpad 24, and/or to display screen 20 for pressure sensing of alphanumeric character entry and user selections. The device drivers 12, R/W drive or interface 14 and network adapter or interface 16 may comprise hardware and software (stored on computer readable storage media 08 and/or ROM 06).

The programs described herein are identified based upon the application for which they are implemented in a specific one of the exemplary embodiments. However, it should be appreciated that any particular program nomenclature herein is used merely for convenience, and thus the exemplary embodiments should not be limited to use solely in any specific application identified and/or implied by such nomenclature.

Based on the foregoing, a computer system, method, and computer program product have been disclosed. However, numerous modifications and substitutions can be made without deviating from the scope of the exemplary embodiments. Therefore, the exemplary embodiments have been disclosed by way of example and not limitation.

It is to be understood that although this disclosure includes a detailed description on cloud computing, implementation of the teachings recited herein are not limited to a cloud computing environment. Rather, the exemplary embodiments are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or data center).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
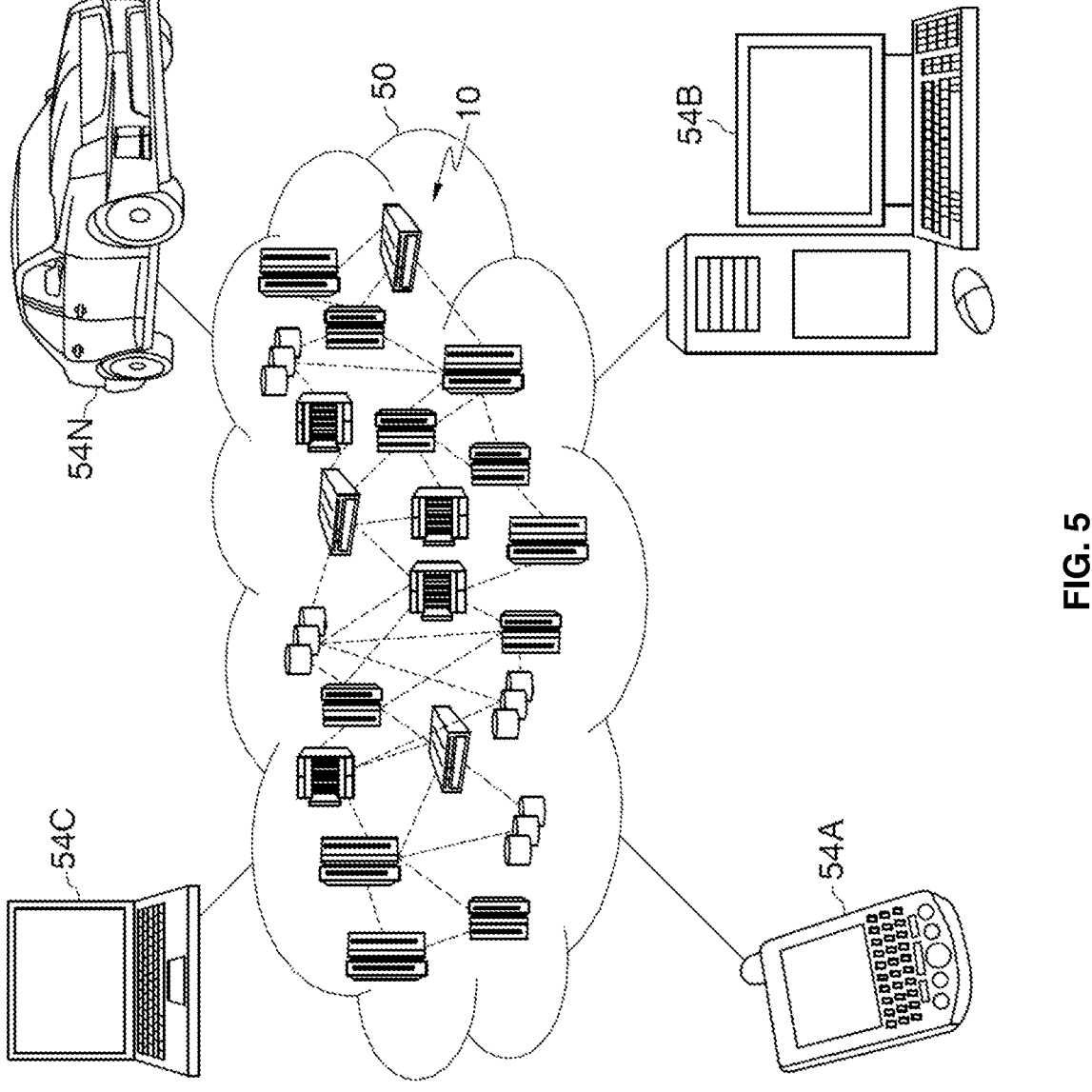
FIG. 5 depicts a cloud computing environment, in accordance with the exemplary embodiments.

Referring now to FIG. 5, illustrative cloud computing environment 50 is depicted. As shown, cloud computing environment 50 includes one or more cloud computing nodes 40 with which local computing devices used by cloud consumers, such as, for example, personal digital assistant (PDA) or cellular telephone 54A, desktop computer 54B, laptop computer 54C, and/or automobile computer system 54N may communicate. Nodes 40 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 40 and cloud computing environment 50 can communicate with any type of computerized device over any type of network and/or network addressable connection (e.g., using a web browser).

Figure 6:
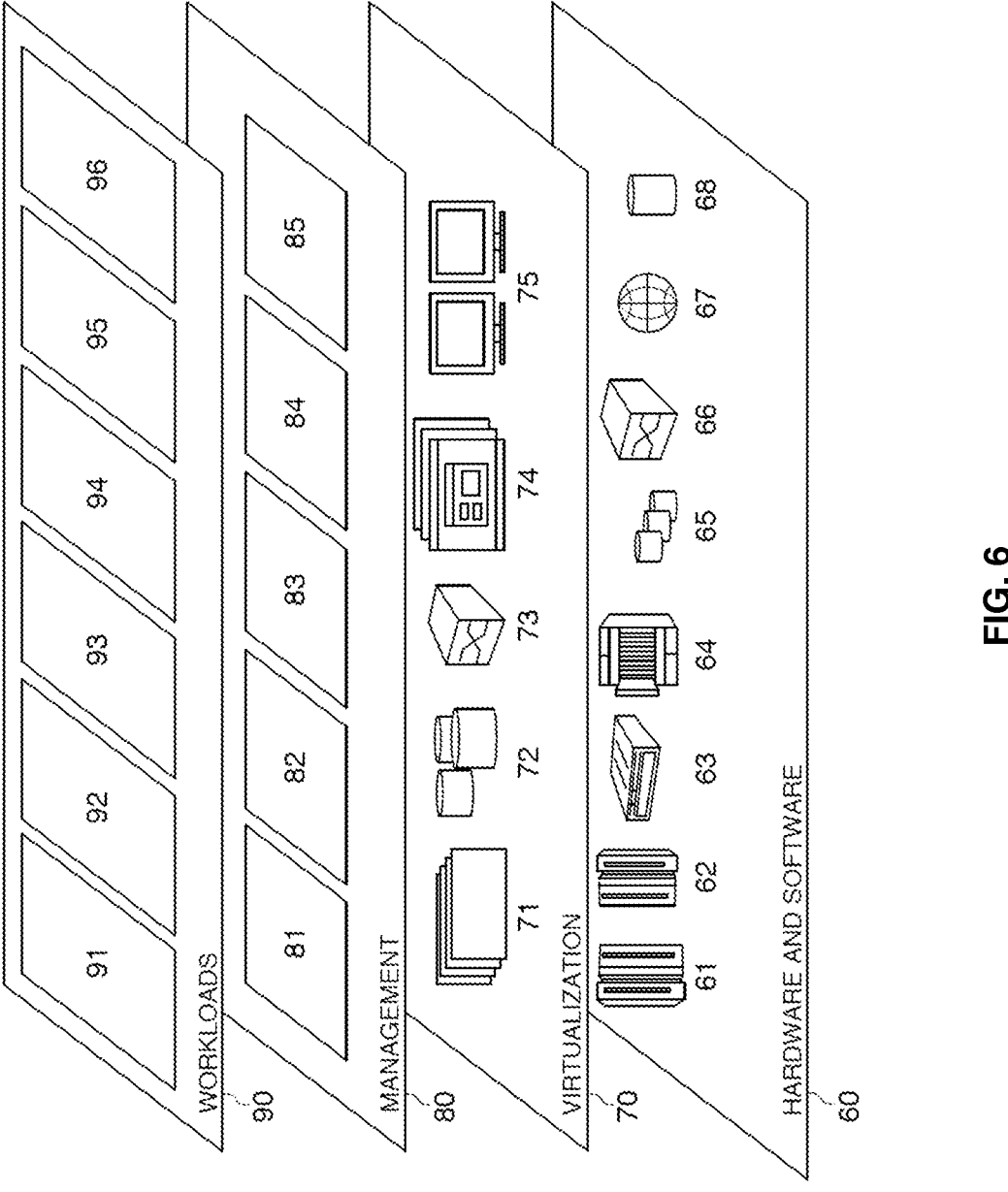
FIG. 6 depicts abstraction model layers, in accordance with the exemplary embodiments.

Referring now to FIG. 6, a set of functional abstraction layers provided by cloud computing environment 50 (FIG. 5) is shown. It should be understood in advance that the components, layers, and functions shown in FIG. 6 are intended to be illustrative only and the exemplary embodiments are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and plaque removal 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A toothbrush for removing dental plaque, the toothbrush comprising:
a first set of light-guiding bristles, the first set having one or more light sources therein, and a second set of light-guiding bristles, the second set having one or more optical sensors therein;
one or more processors, one or more computer-readable memories, and one or more computer-readable storage media; and
program instructions, stored on at least one of the one or more computer-readable storage media for execution by at least one of the one or more processors via at least one of the one or more computer-readable memories to:
capture tooth data based on a difference between light emitted from the one or more light sensors of the first set of light-guiding bristles towards a tooth of a user and light reflected off the tooth of the user captured through the one or more optical sensors of the second set of the light-guiding bristles;
collect tooth brushing data for the user from a dental history or a brushing history;
extract one or more features from the tooth data and the tooth brushing data for the user;
determine a plaque value using a machine learning model that weights the plaque value based on the one or more features, wherein a higher absorption level of the emitted light is associated with a higher plaque value; and
identify a dental plaque location on the tooth based on the plaque value.

2. The toothbrush of claim 1, wherein the program instructions further comprise operations to:

generate a notification for the user of the dental plaque location on the tooth, wherein the notification comprises one or more of: audio, video, touch, and a change in motor speed of the toothbrush; and identify a next dental plaque location on the tooth in response to detecting that the dental plaque has been removed.

3. The toothbrush of claim 1, wherein the program instructions further comprise operations to:

provide real-time brushing guidance to the user; and reward credits to the user for the removal of dental plaque.

4. The toothbrush of claim 1, wherein the program instructions to identify the dental plaque location is further based on using one or more plaque disclosing agents, fluorescent agents, or additive colorings.

5. The toothbrush of claim 1, wherein the one or more features include features selected from a group comprising an amount of light absorption, light intensity, light scattering, light wavelength spectrum, light polarization, brushing history, dental plaque accumulation patterns, locations of dental plaque, amounts of plaque, locations of fillings, locations of stains, discolorations of tooth surfaces, bristle life/effectiveness, effectiveness of brushing, and efficiency of brushing.

* * * * *